(12) United States Patent
Carmichael et al.

(10) Patent No.: US 8,622,614 B2
(45) Date of Patent: Jan. 7, 2014

(54) LOCKING DEVICE FOR MOBILE X-RAY SYSTEM

(75) Inventors: Evan P. Carmichael, West Henrietta, NY (US); Michael P. Urbon, Churchville, NY (US)

(73) Assignee: Carestream Health, Inc., Rochester, NY (US)

( * ) Notice: Subject to any disclaimer, the term of this patent is extended or adjusted under 35 U.S.C. 154(b) by 334 days.

(21) Appl. No.: 13/213,126

(22) Filed: Aug. 19, 2011

(65) Prior Publication Data

US 2012/0045037 A1    Feb. 23, 2012

Related U.S. Application Data

(60) Provisional application No. 61/375,980, filed on Aug. 23, 2010.

(51) Int. Cl.
*H05G 1/02* (2006.01)

(52) U.S. Cl.
USPC .......................................... 378/198; 378/210

(58) Field of Classification Search
USPC .......................................... 378/198, 208, 210
See application file for complete search history.

(56) References Cited

U.S. PATENT DOCUMENTS

| 5,844,961 A | 12/1998 | McEvoy et al. |
| 7,097,355 B2 | 8/2006 | Araki et al. |
| 7,611,282 B2 | 11/2009 | Koren et al. |
| 2008/0209965 A1 | 9/2008 | Maack |
| 2010/0060410 A1 | 3/2010 | Wirth |

FOREIGN PATENT DOCUMENTS

| WO | WO2007/078684 | 7/2007 |
| WO | WO 2007/139638 | 12/2007 |

*Primary Examiner* — Jurie Yun

(57) ABSTRACT

A mobile radiography apparatus has a moveable (e.g., wheeled) transport frame and an adjustable column mounted at the frame. A boom apparatus supported by the adjustable column can support an x-ray source and can be coupled to a optional second display (also adjustably mounted). Embodiments of methods and/or apparatus by which mobile radiography carts can provide a securable storage for at least one radiographic detector by blocking at least a portion of a path traveled by the at least one radiographic detector when removed from storage at the mobile radiography apparatus.

19 Claims, 22 Drawing Sheets

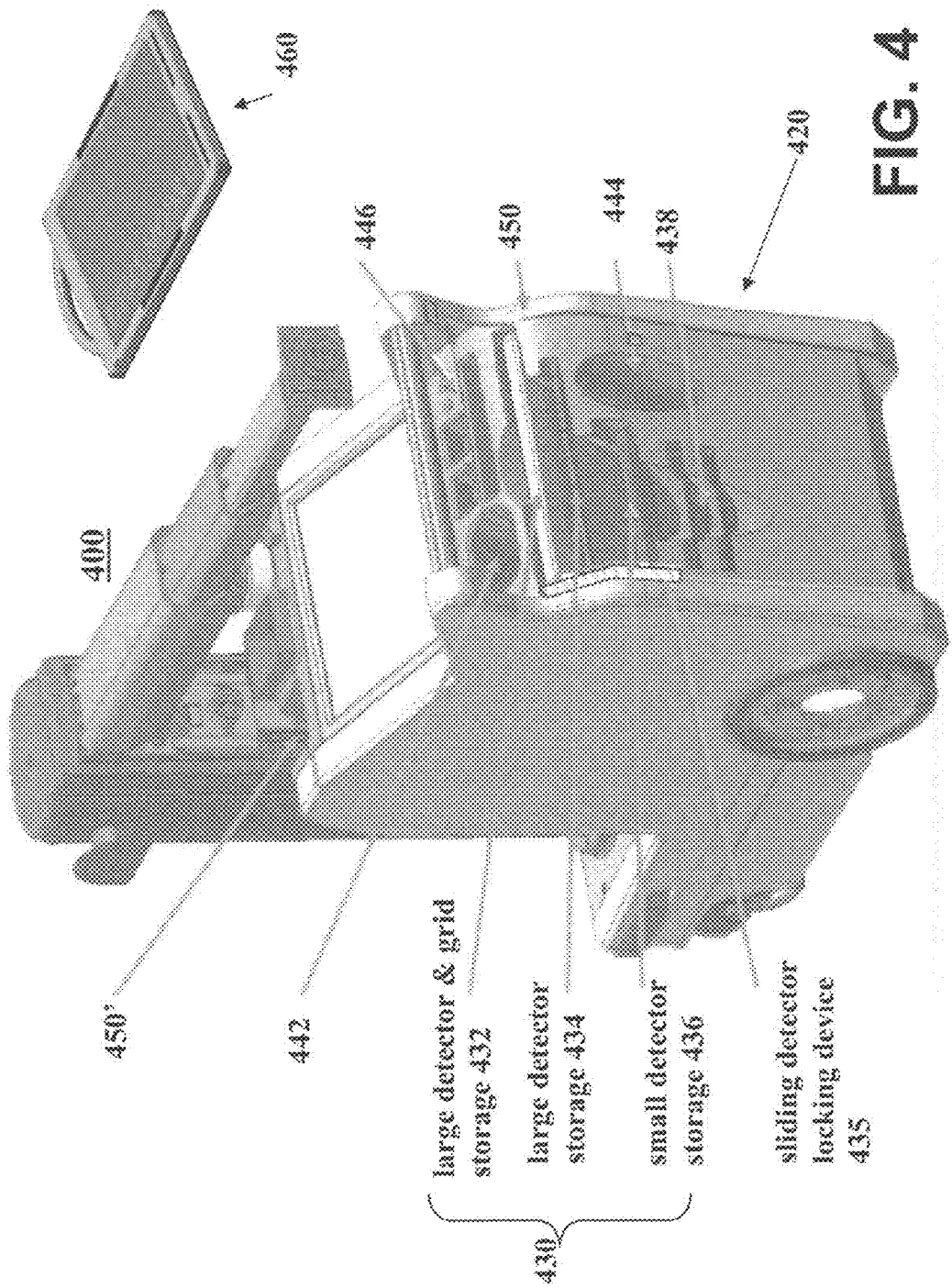

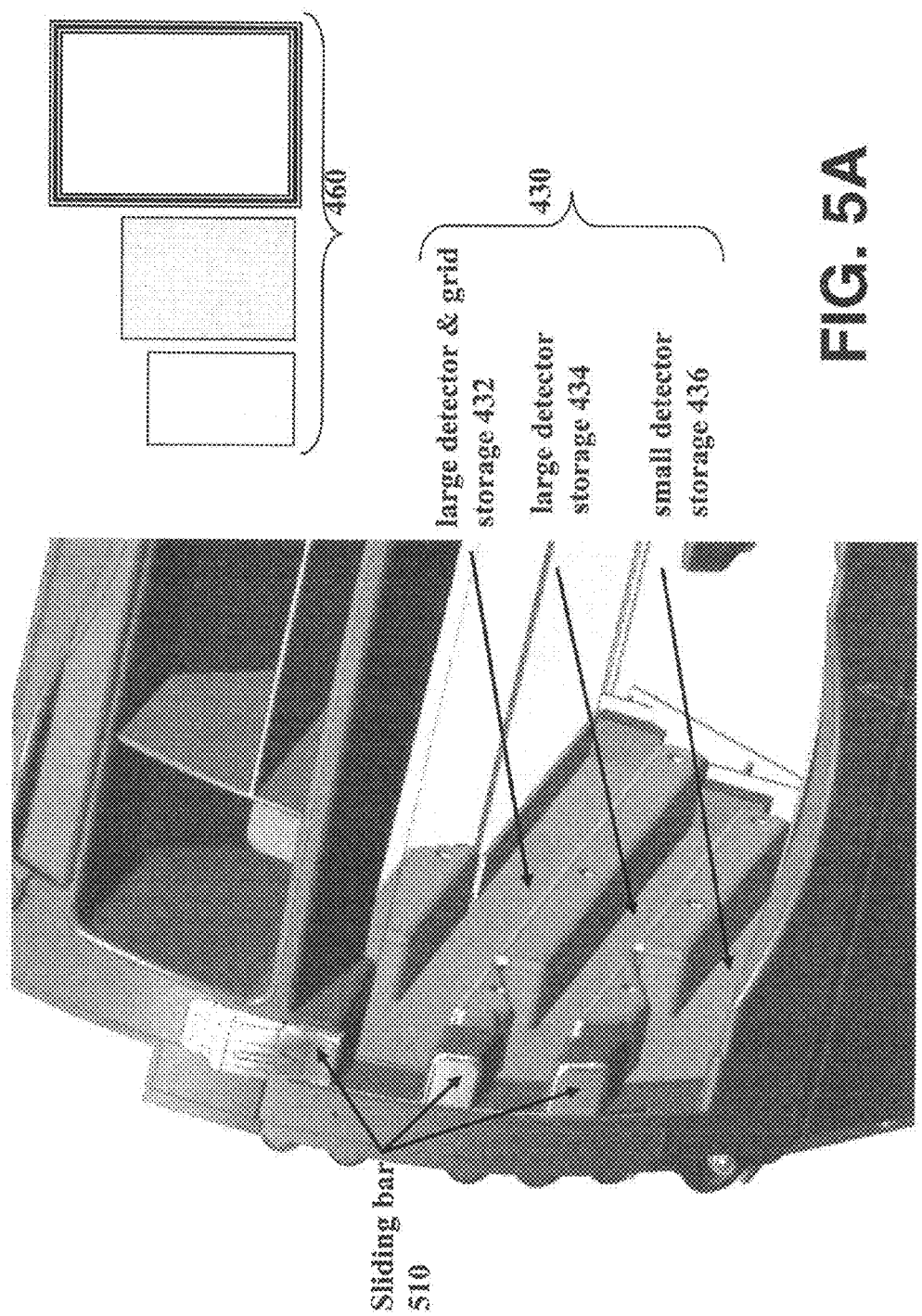

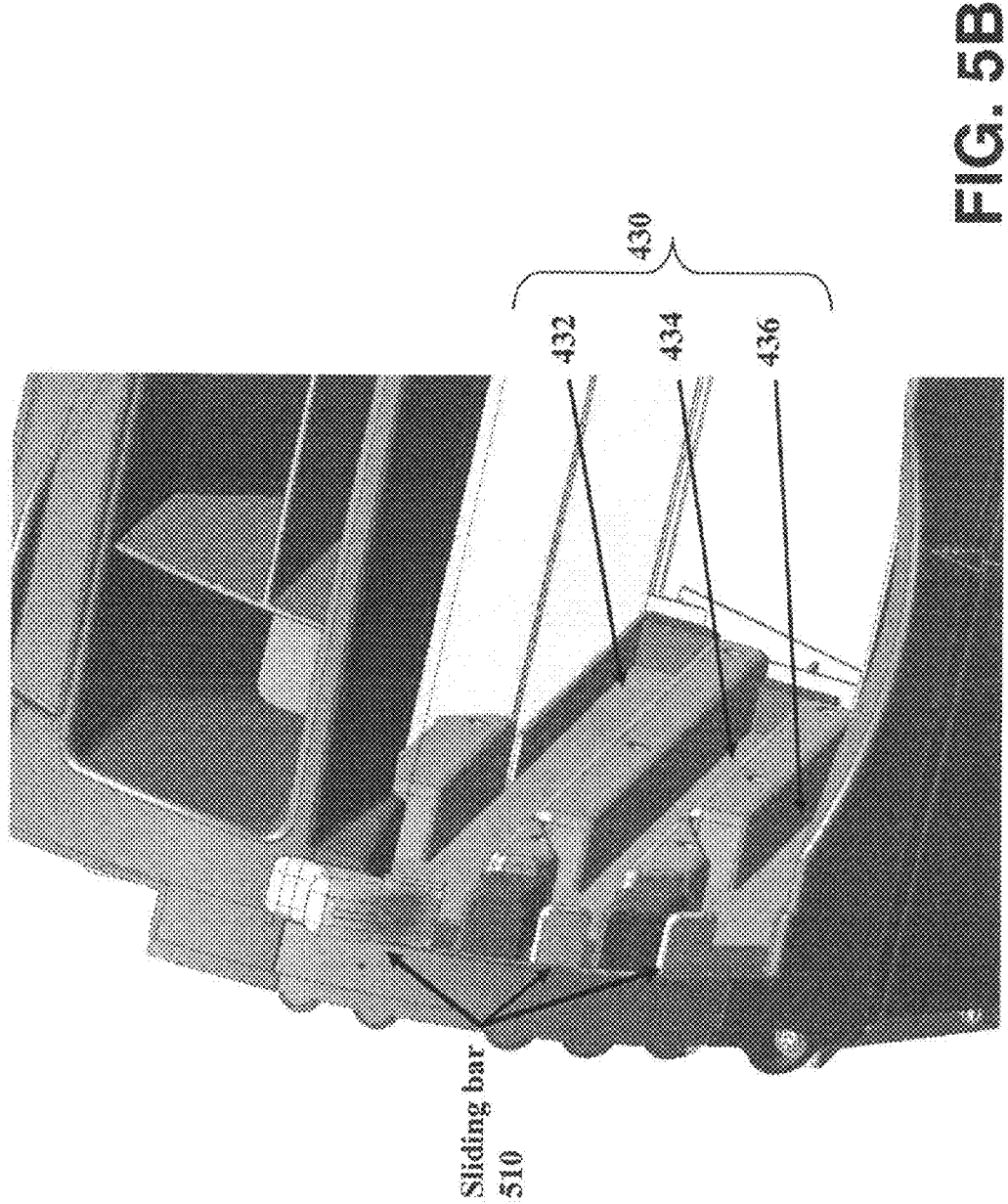

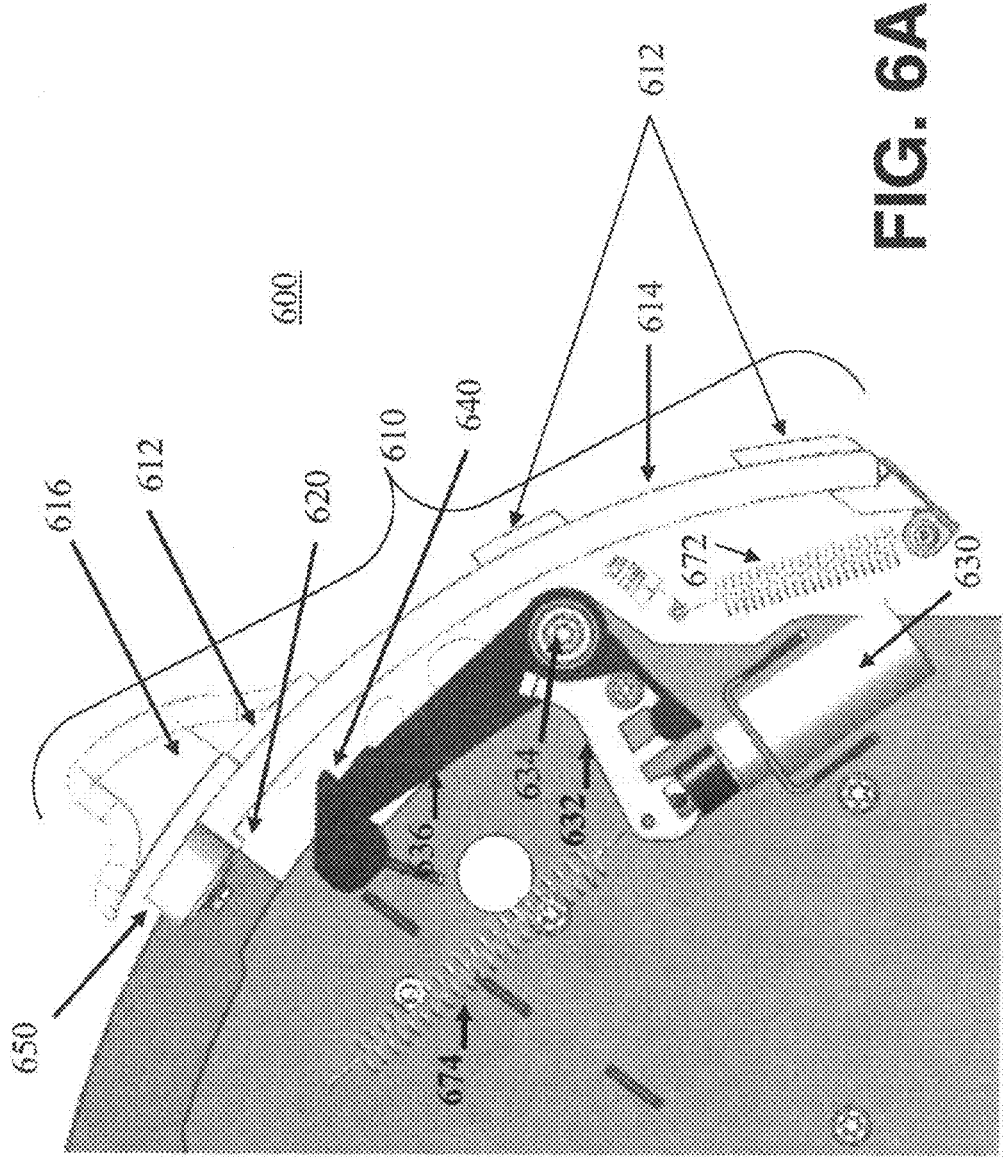

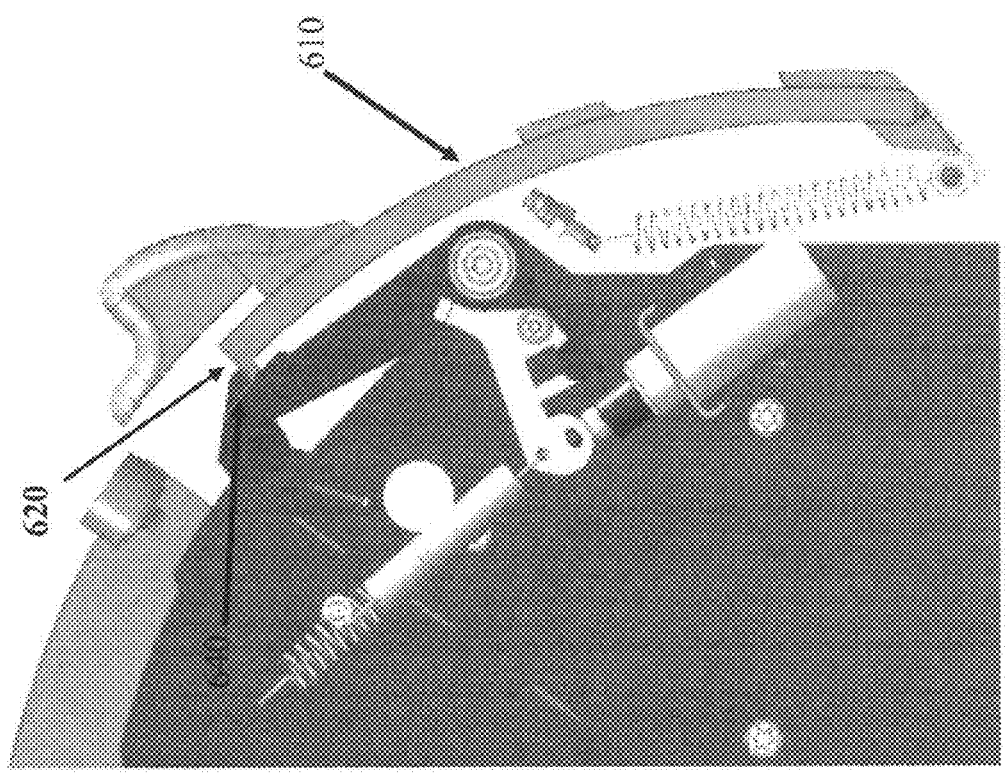

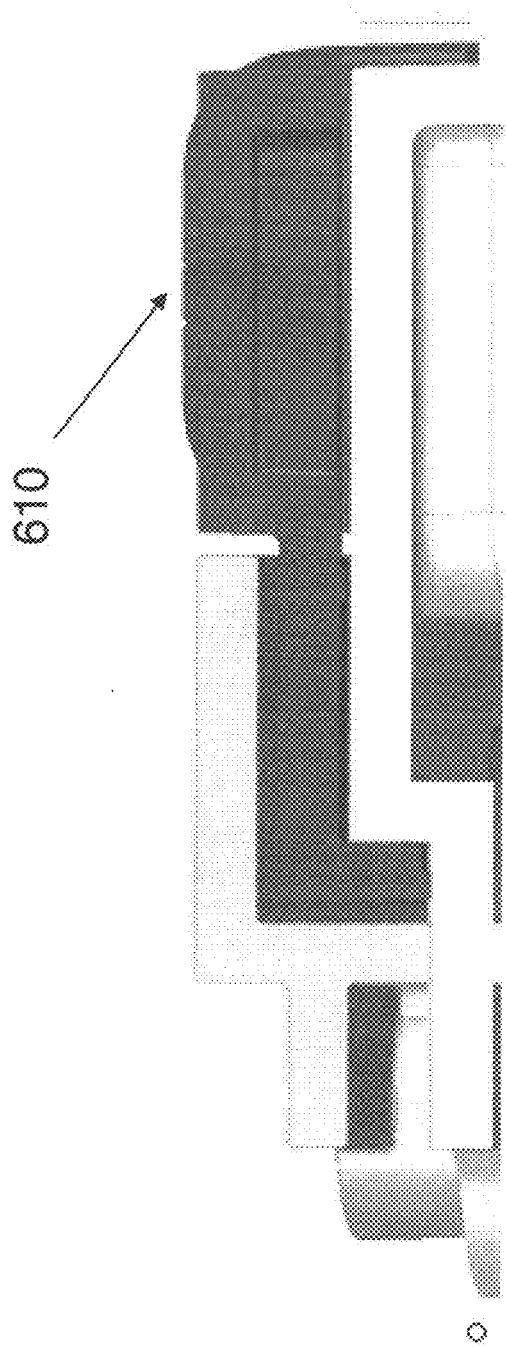

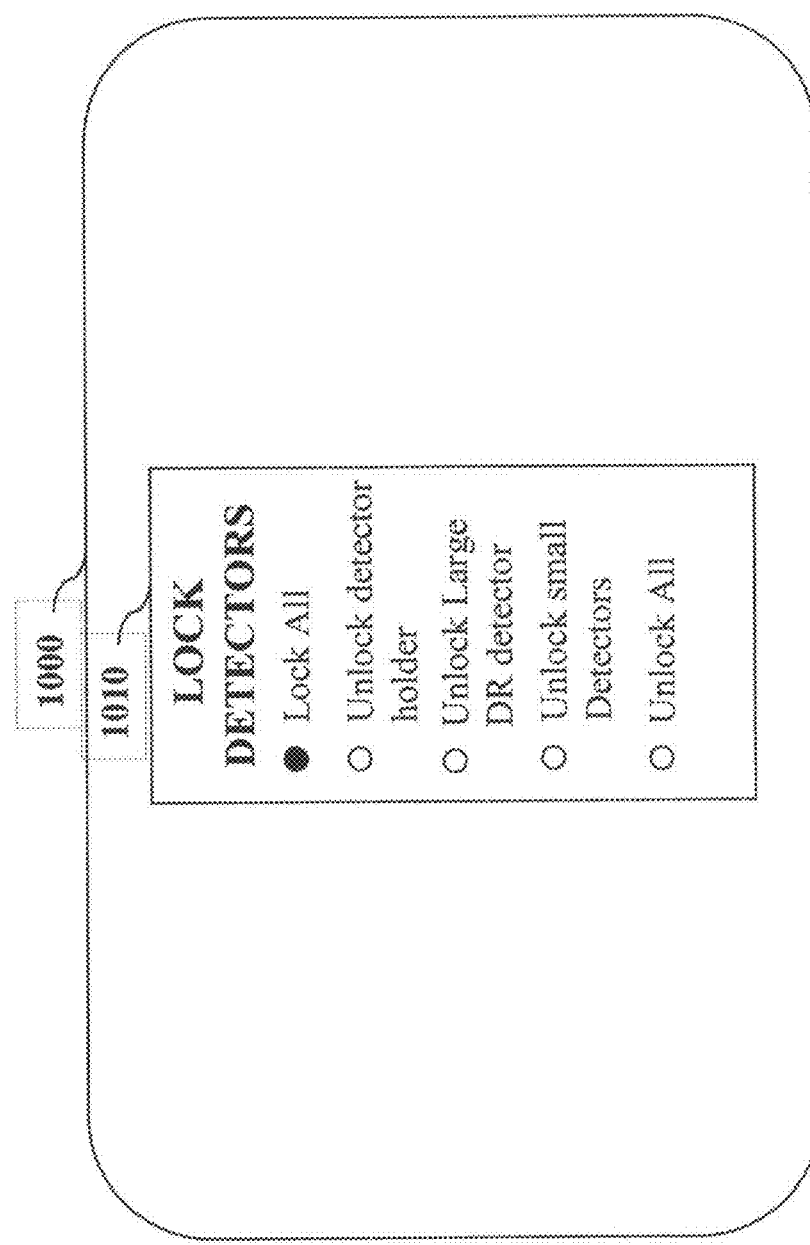

| | Patient Name | Location | Exam | Exam Time |
|---|---|---|---|---|
| ● | James Johnson | Rm 203 | Portable Chest | 4/11/2010 11:23:51 AM |
| ● | Fred Smith | Rm 224 | Knee | 4/11/2010 11:24:12 AM |
| ● | Fred Jones | Rm 245 | Portable Chest | 4/11/2010 11:23:44 AM |
| ● | Scott Smith | Rm 252 | Portable Hip | 4/11/2010 11:24:05 AM |
| ● | John Jones | Rm 483 | Portable Hip | 4/11/2010 11:22:48 AM |
| ● | Bill Miller | Rm 508 | Portable Hip | 4/11/2010 11:23:37 AM |
| ● | Bill Smith | Rm 572 | Knee | 4/11/2010 11:23:30 AM |
| ● | Bill Miller | Rm 778 | Portable Chest | 4/11/2010 11:23:16 AM |
| ● | Mike Jones | Rm 884 | Knee | 4/11/2010 11:23:23 AM |
| ● | Robert Jones | Rm 944 | Portable Hip | 4/11/2010 11:23:02 AM |
| ● | Fred Johnson | Rm 993 | Knee | 4/11/2010 11:23:58 AM |

LOCKING DEVICE FOR MOBILE X-RAY SYSTEM

CROSS REFERENCE TO RELATED APPLICATIONS

Priority is claimed from commonly assigned, U.S. provisional patent application Ser. No. 61/375,980, filed Aug. 23, 2010, entitled "LOCKING DEVICE FOR MOBILE X-RAY SYSTEM", in the name of Evan P. Carmichael, the disclosure of which is incorporated by reference.

FIELD OF THE INVENTION

The invention relates generally to the field of medical imaging, and in particular to portable radiographic imaging apparatus. More specifically, the invention relates to a mobile radiography apparatus including securable access to at least one portable radiographic detector.

BACKGROUND

Mobile carts are employed in medical facilities to move medical equipment between locations. One type of mobile cart includes an x-ray source used to capture (e.g., digital) x-ray images on x-ray detector. Medical x-ray images can be captured using various digital or analog techniques.

Refer also to U.S. Pat. No. 7,611,282 (Koren) and WO 2007/139638 (Jadrich), and WO 2007/078684 (Dhurjaty), and U.S. Pat. No. 5,844,961 (McEvoy).

Mobile x-ray apparatus are of particular value in intensive care unit (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

However, there is a need for improvements in mobile x-ray apparatus design to allow such devices to be more easily transported, deployed and/or operated.

SUMMARY OF THE INVENTION

An aspect of this application is to advance the art of mobile radiography.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which mobile radiography carts can be modified to provide secured storage for at least one radiographic detector.

Another aspect of the application is to provide embodiments of lockable detector storage area devices that can move between a locking position restricting removal of at least one detector and an unlocked position allowing removal at least one detector(s) from a storage area of a mobile x-ray system.

Another aspect of the application is to provide methods and/or apparatus by which mobile radiography carts can provide embodiments of lockable detector storage area devices that can move between a single locking position or a plurality of different positions restricting removal of at least one detector and an unlocked position or plurality of different unlock positions allowing removal detector(s) from a storage area of a mobile x-ray system. Embodiments of lockable detector storage area devices can be configured to selectively lock (or unlock) individual ones or various combinations of detector storage slots.

In accordance with one embodiment, the invention can provide a mobile radiography apparatus that can include a moveable transport frame; an adjustable support structure coupled to the moveable transport frame; an x-ray source coupled to the adjustable support structure; and a lockable detector storage unit configured to securely store at least one radiographic detector at the mobile radiography apparatus, where the lockable storage device can include at least one recess configured to store the at least one radiographic detector, and a securing device that can include, a sliding member slidingly attached to the moveable transport frame to reciprocally move along a first direction, a first engaging portion coupled to the sliding member, an actuator configured to move between a first position and a second position, a second engaging portion coupled to the actuator, where the second engaging portion is disengaged from the first engaging portion when the actuator is in the second position.

In accordance with one embodiment, the present invention can provide a mobile x-ray radiographic apparatus can include a moveable transport frame; an adjustable support structure coupled to the moveable transport frame; an x-ray source coupled to the adjustable support structure; and a lockable detector storage unit configured to lockably store at least one portable detector at the mobile x-ray radiographic apparatus, where the lockable storage device can include at least one recess configured to store the at least one remote digital detector, and a securing device that can include an elongated bar slidingly attached to the moveable transport frame to reciprocally move along a first direction between a first position and a second position and configured to include at least one projection, a first engaging portion coupled to the sliding bar, a second engaging portion, and an actuator coupled to and configured to move the second engaging portion, where the securing device is configured to allow access to the at least one recess in the first position, where the securing device is configured to secure the at least one recess in the second position, and where the second engaging portion is positioned to engage the first engaging portion when the securing device is in the second position.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 4 is a diagram that illustrates an embodiment of a locking device for mobile radiographic system according to the application.

FIGS. 5A-5B are diagrams that illustrate a perspective view of an embodiment of a locking device for mobile radiographic system according to the application.

FIGS. 6A-6B are diagrams that illustrate a side view of an embodiment of a locking device for mobile radiographic system according to the application.

FIGS. 7C-7D are diagrams that illustrate an embodiment to attach a sliding detector locking device for mobile radiographic system according to the application.

FIG. 10 is a diagram that illustrates an embodiment of a lockable detector storage area authorization screen according to the application.

FIGS. 11-14 are diagrams that illustrate exemplary functions implemented at an embodiment of a second display of a mobile x-ray imaging apparatus.

DESCRIPTION OF EXEMPLARY EMBODIMENTS

Figure 1:
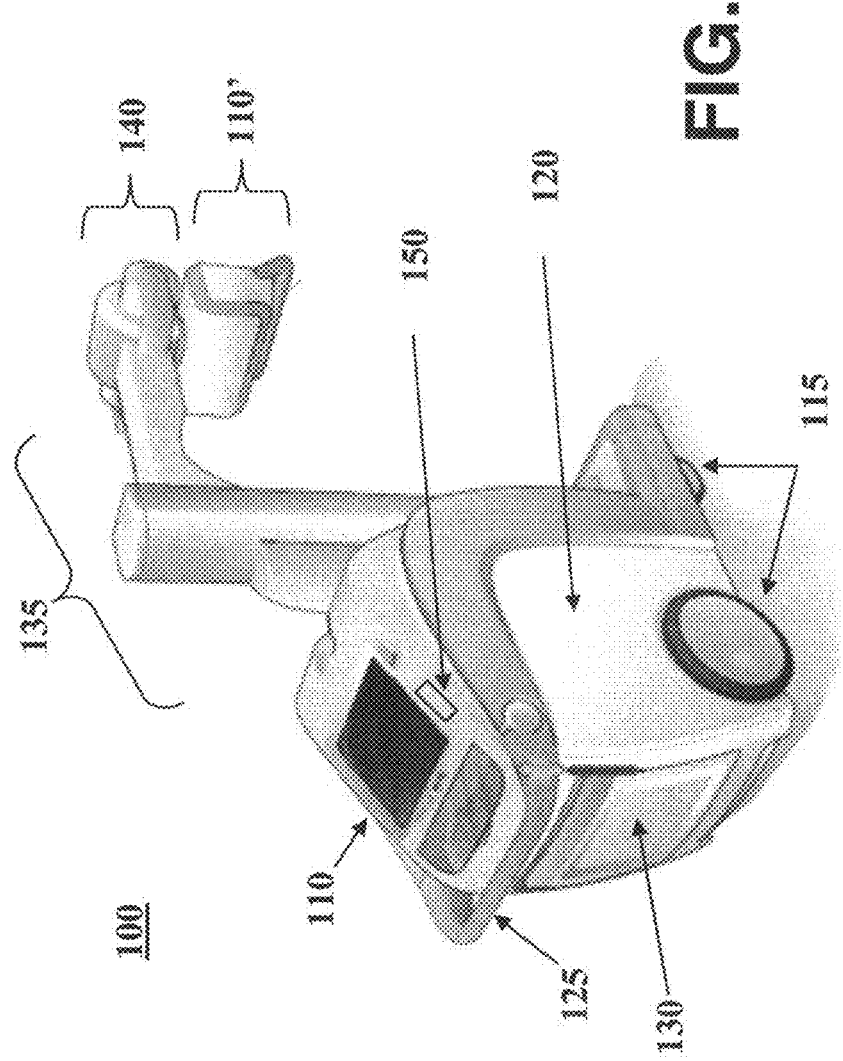
FIG. 1 is a diagram that shows a perspective view of a mobile radiography unit according to one embodiment of the application.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

FIG. 1 is a diagram that shows a perspective view of a mobile radiography unit that can include a locking device for portable radiographic detectors or flat panel detectors according to embodiments of the application. The exemplary mobile x-ray or radiographic apparatus of FIG. 1 can be employed for computed radiography (CR) and/or digital radiography (DR). As shown in FIG. 1, a mobile radiography apparatus 100 can include a moveable transport frame 120 that includes a first display 110 and an optional second display 110' for display relevant information such as obtained images and related data. As shown in FIG. 1, the second display 110' can be pivotable mounted at the x-ray source 140 to be viewable/touchable from a 360 degree area.

The displays 110, 110' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography cassettes. The area/holder can be storage area 130 (e.g., disposed on the frame 120) configured to removably retain at least one digital radiography (DR) detector. The storage area 130 can be configured to hold a plurality of detectors and can also be configured to hold one size or multiple sizes of DR detectors.

Mounted to frame 120 is a support column 135 that supports an x-ray source 140, also called an x-ray tube, tube head, or generator that can be mounted to the support member 135. In the embodiment shown in FIG. 1, the support member (e.g., column 135) can include a second section that extends outward a fixed/variable distance from a first section where the second section is configured to ride vertically up and down the first section to the desired height for obtaining the image. In another embodiment, the tube head or x-ray source 140 can be rotatably coupled to the support column 135. In another exemplary embodiment, an articulated member of the support column that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions.

Figure 2:
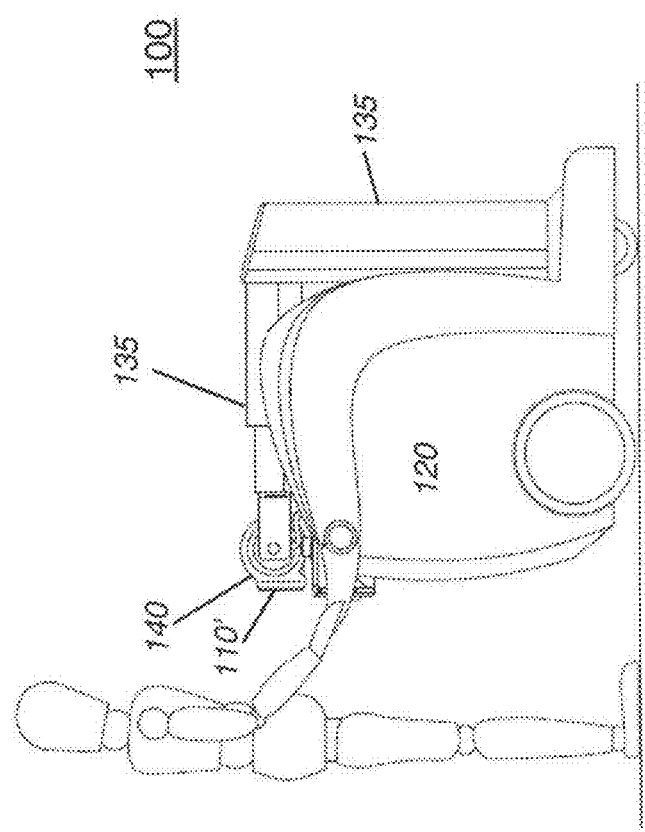
FIG. 2 is a diagram that shows a perspective view of a mobile radiography unit of FIG. 1 positioned for travel.

As shown in FIG. 2, for ease during transport of the mobile radiographic apparatus 100, the support member 135 and x-ray source 140 can be arranged close to frame 120. As shown in FIG. 2, the second display 110' can be in a viewable position (e.g., operable) during transport of the mobile radiographic apparatus 100. When the mobile radiographic apparatus 100 is to be used, the support member 135 and x-ray source 140 can be extended from the frame 120 for proper positioning (e.g., by the operator, a user, or x-ray technician) and the second display 110' moved to viewable position such as shown in FIG. 1.

Figure 3:
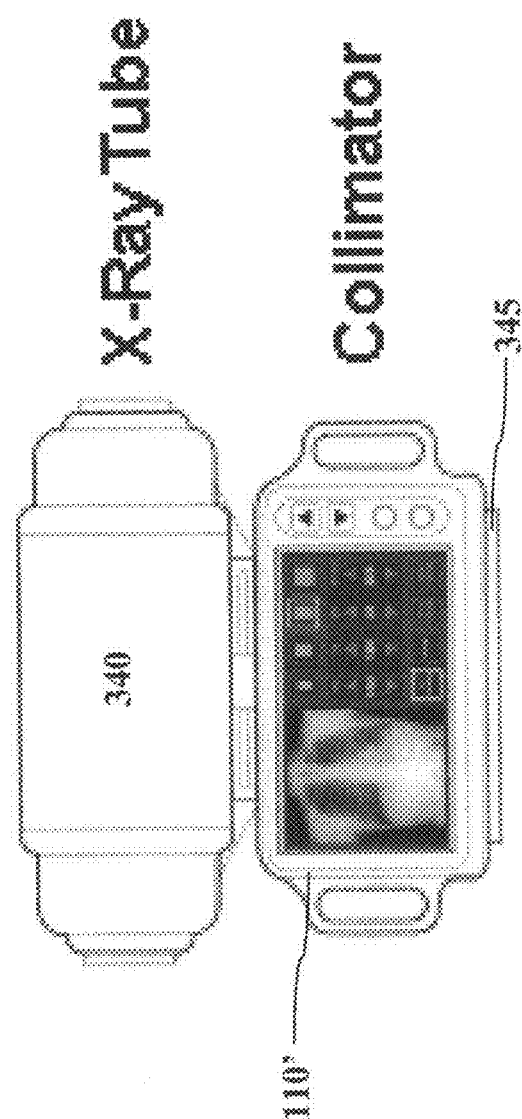
FIG. 3 is a diagram that shows an exemplary embodiment of a display/monitor as a second display mounted to a boom assembly of a mobile radiography unit according to the application.

FIG. 3 is a diagram that shows an exemplary embodiment of a display/monitor as a second display mounted to a boom assembly of a mobile radiography unit according to the application. As shown in FIG. 3, the second display 110' can be mounted to a collimator 345 of an x-ray source 340 of a support member 135 of a mobile radiography unit. In one embodiment, the collimator 345 can be rotably mounted to the x-ray source 340 so that the collimator 345 (e.g., second display 110') can swivel at least 90 degrees, at least 180 degrees or 360 degrees. As shown in FIG. 3, the second display 110' is coupled to a plurality of handles for ease of positioning. Alternatively, the second display 110' can be mounted to (e.g., rotatably) an x-ray source 340 above a collimator 345 of a boom assembly of a mobile radiography unit.

Embodiments according to the application relate to a locking device for a mobile x-ray system. The detector is an expensive component that can be readily removed and/or moved to different locations. To ensure that the detector resides with the mobile x-ray system, a locking device can be employed. Embodiments of locking devices according to application can provide securable storage for removable radiographic detectors such as flat panel detectors, remote detectors, digital radiographic (DR) detectors, portable wireless DR detectors and the like that can be used with a mobile radiographic system.

According to exemplary embodiments shown in the application figures, each detector can be disposed in a storage area. The storage area is shown as slots within the base of the mobile x-ray system. However, embodiments of detector storage areas are not intended to be so limited. The device/lock can cover a portion of the opening of the storage area to restrict removal of the detector from its storage location. As shown in at least one figure, a single device can restrict the removal of three detectors since the device/lock can cover a portion of the openings of the three storage areas. An alternative device can be configured to lock a single detector. Alternatively, multiple devices/locks can lock one or more detectors. The device can be removed by sliding or lifting away from the opening of the storage area(s), thereby providing access to the detector(s) in its storage location.

According to exemplary embodiments, at least one removable detector can be securably stored in a storage area at the mobile x-ray system by a securing apparatus or a locking device that can cover (e.g., movably, reciprocally, slideably) a portion of an opening of the storage area to restrict removal of the detector from its storage location. In one embodiment, a securing apparatus or a locking device can move between a first position restricting removal of at least one detector and a second position allowing removal of at least one detector from a storage area of a mobile x-ray system. Locking device embodiments can restrict removal of one or more radiographic detectors that have different sizes (e.g., 10 cm by 20 cm, 24 cm by 30 cm, 45 cm by 45 cm, etc.). In one embodiment, the storage area can be recesses (e.g., slots, grooves, bins, mounts or the like) at or within a base, a movable bin or a fixed bin of the mobile x-ray system.

FIG. 4 is a diagram that illustrates an embodiment of a securing apparatus or a locking device for mobile radiographic system according to the application. As shown in FIG. 4, a mobile radiography apparatus 400 can include a moveable transport frame 420 that includes storage area 430 and locking device 435. The storage area 430 can include a plurality of individual securable portions or slots such as detector holder storage or large detector and grid storage 432, large detector storage 434, and/or small detector storage 436 that can be secured using locking device 435. Exemplary detector holders can include a detector with/without a grid and/or additional detector accessories such as but not limited to additional antenna, power supply or additional electronics. Storable detector holders can include just the holder without the detector. The locking device 435 can reciprocally move between a first position (e.g., unlocked) where detectors can be removed from the storage area and a second position (e.g., locked) where detectors can not be removed from the storage area. In one embodiment, the storage area 430 can include an area or battery charge slots 438 where at least one battery for use with or removed from detectors 460 can be re-charged by the mobile radiography apparatus 400. Additional storage areas for materials at the mobile radiography apparatus 400 can include storage 442 (e.g., for rubber gloves), bag storage area 444, and additional storage 446. The mobile radiography apparatus 400 can also include a wired prep/expose control 450 and a remote prep/expose control 450'.

As shown in FIG. 4, a single locking device 435 can cover a left side portion of openings of three storage areas. Alternatively, the locking device 435 can be positioned along a right side or cross between left and right edges of the storage area 430. As shown in FIG. 4, the sliding detector locking device 435 can be a contiguous integral device. Alternatively, the sliding detector locking device 435 can be a discontinuous locking device (e.g., two sliding members that meet in between a top edge and a bottom edge of the storage area in the locked position) or a plurality of sliding locking device 435, each for one or more detector storage portions such as storage 432, 434, 436.

FIGS. 5A-5B are diagrams that illustrate an embodiment of a securing apparatus or a locking device for mobile radiographic system according to the application. FIG. 5A shows a sliding detector locking device in a first, open or unlocked (e.g., unengaged) position and FIG. 5B shows a sliding detector locking device in a second, closed or secured (e.g., engaged) position.

As shown in FIGS. 5A-5B, a sliding detector locking device 500 an can include sliding bar 510 that can be attached to the moveable transport frame 420 by one or more layers of the movable transport frame 420 or fasteners such as bolts, screws, rivets, adhesives or the like (not shown). Exemplary fasteners can fixedly attach the sliding bar 510 to the moveable transport frame 420 so that the sliding bar 510 can move between at least a first position (e.g., FIG. 5A) and a second position (e.g., FIG. 5B). In one embodiment, the sliding bar 510 has a curve to match a surface of the transport base of the mobile x-ray apparatus. Alternatively, the sliding bar 510 can be tiered, stepped or straight preferably to correspond to surface openings of storage portions of the storage area 430. In one embodiment, openings to storage 432, 434, 436 can be arranged in a waterfall (e.g., offset in 2 or 3 dimensions descending relative to each other) along a portion of the surface of the movable transport frame 420. As shown in FIG. 5B, the sliding bar 510 (e.g., itself or securing tabs, projections or portions thereof) in a locked position can prevent removal of various detectors 460 in storage 432, 434, 436 from the mobile x-ray system 400. The sliding bar 510 is shown as an elongated bar with locking projections, however, embodiments are not intended to be so limited as other shapes and/or objects such as rods, covers, retractable pins or the like can be used.

FIGS. 6A-6B are diagrams that illustrate a cross-sectional view of an embodiment of a locking device for mobile radiographic system according to the application. FIG. 6A shows a sliding detector locking device in a first or unlocked position and FIG. 6B shows a sliding detector locking device in a second or locked position.

As shown in FIGS. 6A-6B, an exemplary embodiment of a sliding detector locking device 600 can include sliding bar 610, a first engaging member 620 coupled to the sliding bar 610, a first urging member 630 and a second engaging portion 640 coupled to the first urging member 630. The sliding bar 610 can include locking projections 612, recesses 614, an optional handle 616 and the first engaging portion 620. The first urging member 630 can be coupled (e.g., rigidly) to the second engaging portion 640 and can operate to reciprocally move the second engaging portion 640 to a position in a path of movement of the first engaging portion 620 and to disengage (e.g., move away from) the first engaging portion 620. Alternatively, the first urging member 630 can operate to reciprocally move the second engaging portion 640 to an engaged position and a disengaged position in coordination with or cooperatively with the first engaging portion 620. Various urging devices such as the first urging member 630 can operate mechanically (e.g., springs, elastic members, etc.) or electrically (e.g., motors and gear/cam assemblies, stepper mechanisms, etc.). As shown in FIGS. 6A-6B, the first urging member 630 can be an electric solenoid and can be rotatably connected to the second engaging portion 640 by a first arm 632, pivoting connection 634 and second arm 636.

As shown in FIG. 6A, the second engaging portion 640 is preferably positioned in a sliding path of the first engaging portion 620, which can first strike (and move along) a sloped face 642 and then a securing face 644 of the second engaging portion 640 as the sliding detector locking device 600 travels from an unlocked position (FIG. 6A) to a locked position (FIG. 6B). As shown in FIG. 6B, a securing face 644 of the second engaging portion 640 can engage a securing face 624 of the first engaging portion 620 when the sliding detector locking device 600 is in a locked position.

Figure 7A:
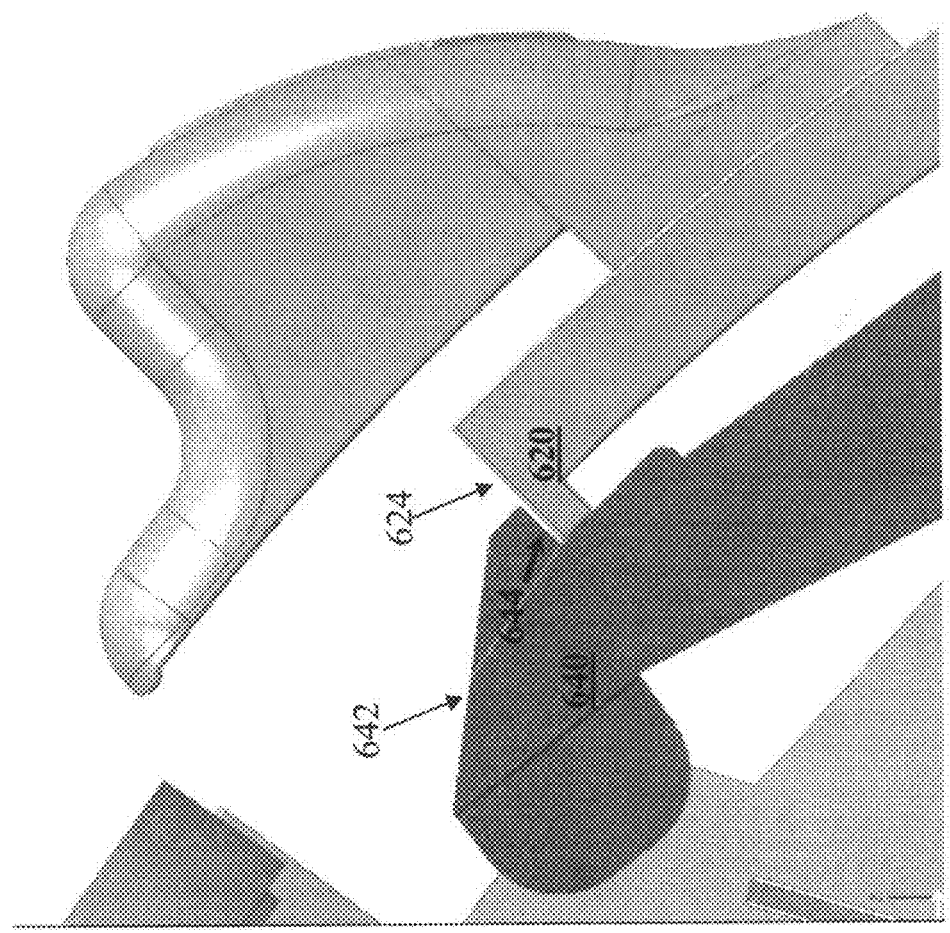
FIG. 7A is a diagram that illustrates a side view of an embodiment of an engaged surface for a locking device for mobile radiographic system according to the application.
Figure 7B:
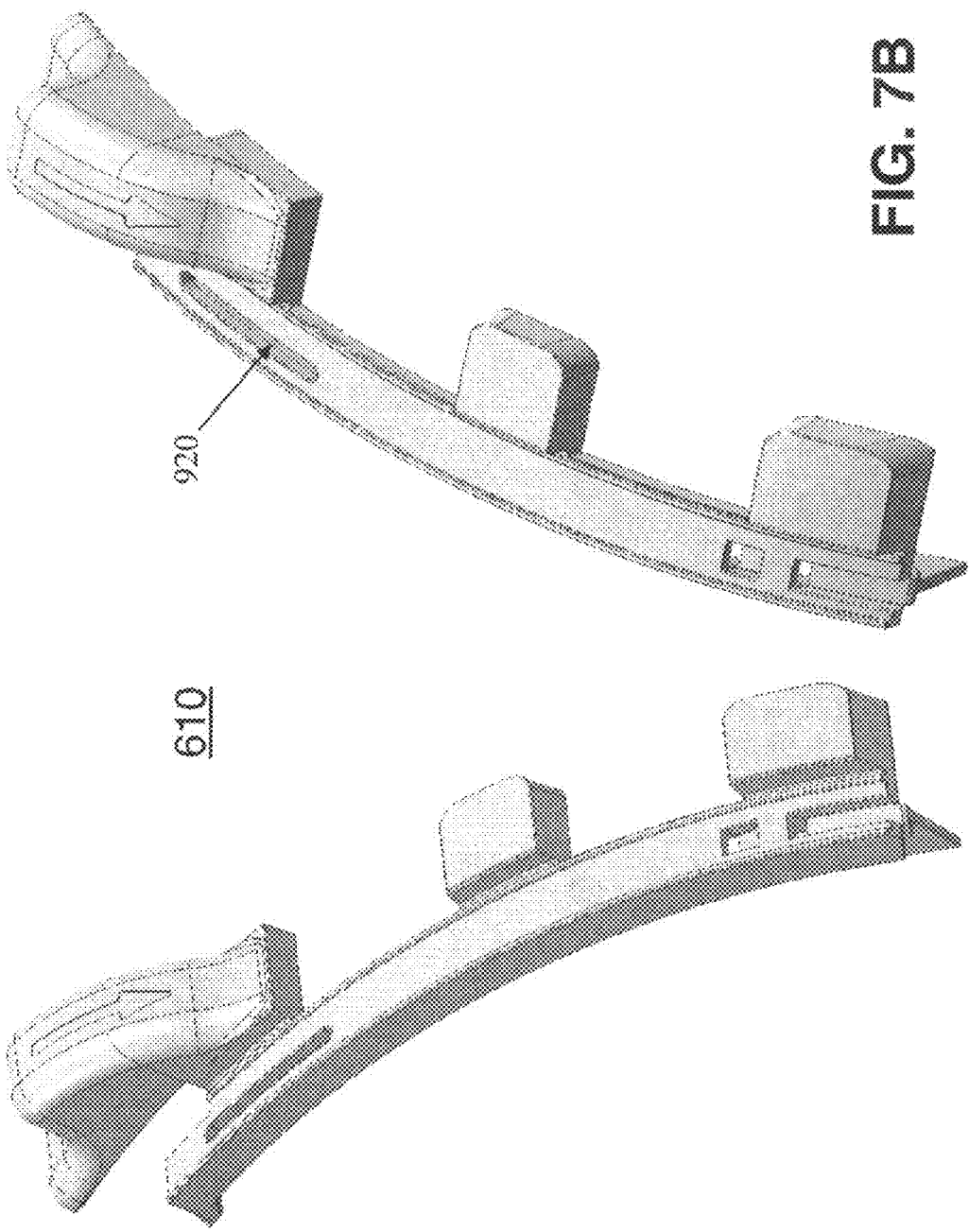
FIG. 7B is a diagram that illustrates an embodiment of a sliding bar for a locking device for mobile radiographic system according to the application.
Figure 7C:
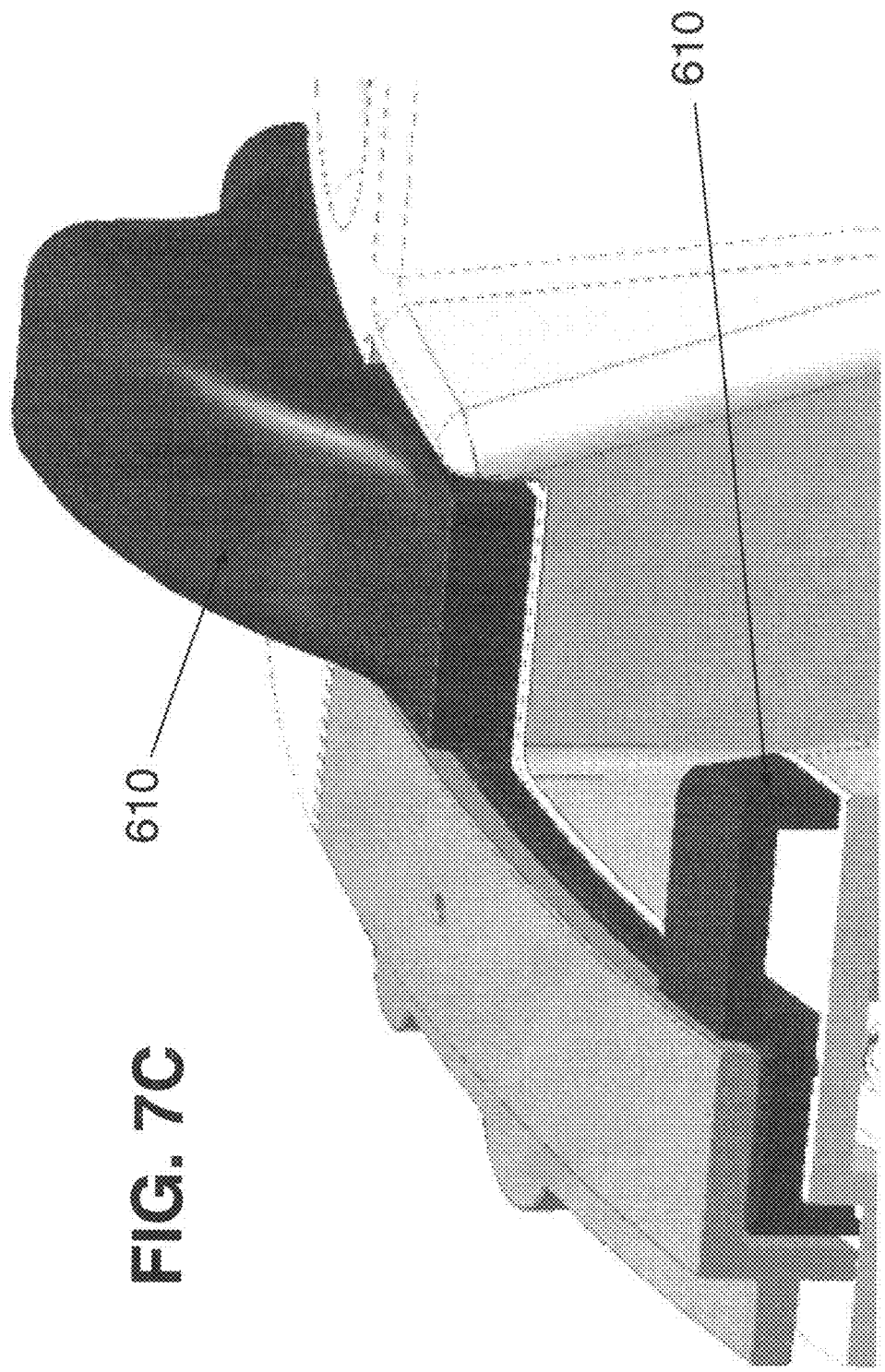

Exemplary securing faces 624, 644 are shown as matched vertical faces, however embodiments of the application are not intended to be so limited. For example, securing faces 624, 644 can be configured with corresponding shapes to ease movement into and/or out of an exemplary engaged position shown in FIG. 7 or to increase a force needed to escape the engaged position. Thus, exemplary securing faces 624, 644 can be linear, non-linear, tiered, interlocking, stepped, etc.

Additional optional secondary urging members can include a bar urging member 672 that can operate to apply force to move the sliding bar 610 toward or to the first or unlocked position and a second engaging portion urging member 674 that can operate to urge the second engaging portion 640 toward or to rest against a lower side of the sliding bar 610.

Exemplary operations for the sliding detector locking device 600 to secure one or more detectors in the storage area of a mobile x-ray apparatus will now be described. A default position of the sliding detector locking device 600 can be in the first or unlocked position shown in FIG. 6A. An operator (e.g., x-ray technician) can load detectors into one or more storage slots of the storage area and manually slide the sliding bar 610 to the second or locked position. Preferably, the movement of the sliding bar 610 to the locked position can cause the second engaging portion 640 to engage the first engaging portion 620. For example, responsive to the manual operator action to move the sliding bar 610, the first engaging portion 620 can slide along the sloped face 642 and drop into a secured relationship where the securing face 644 of the second engaging portion 640 engages the securing face 624. When the operator releases the sliding bar 610, the bar urging member 672 and the second engaging portion urging member 674 can apply force to secure the sliding detector locking device 600 in the locked position where the second engaging portion 640 is engaged to the first engaging portion 620 at matching surfaces (e.g., flat or vertical) as shown in FIG. 6B.

To unlock the sliding detector locking device 600, the operator can select an unlock detector operator action on a display device of the mobile x-ray apparatus. Responsive to the unlock operator action, the first urging member 630 can be activated to operate as an actuator to move (e.g., pull) the second engaging portion 640 to the unlocked position where the second engaging portion 640 is not engaged to the first engaging portion 620 as shown in FIG. 6A and the bar urging member 672 can move the sliding bar 610 along the surface of the moveable transport frame 420 to abut stopper 650. Then, the first urging member 630 can be de-activated to allow the second engaging portion urging member 674 to apply force to re-position the second engaging portion 640 in the sliding path (e.g., abut a lower surface of the sliding bar 610) of the first engaging portion 620.

According to embodiments of the application, de-activation (or activation) of a device/lock (e.g., sliding detector locking device 600) can be variously accomplished by operator log in or sign onto the mobile radiographic apparatus 400, entering a password into the system (e.g., via a keyboard or touch screen), remotely by a fob, and/or by swiping a passkey or ID card (e.g., having a magnetic strip) through a reader (e.g., magnetic) attached to the mobile x-ray system).

Figure 8:
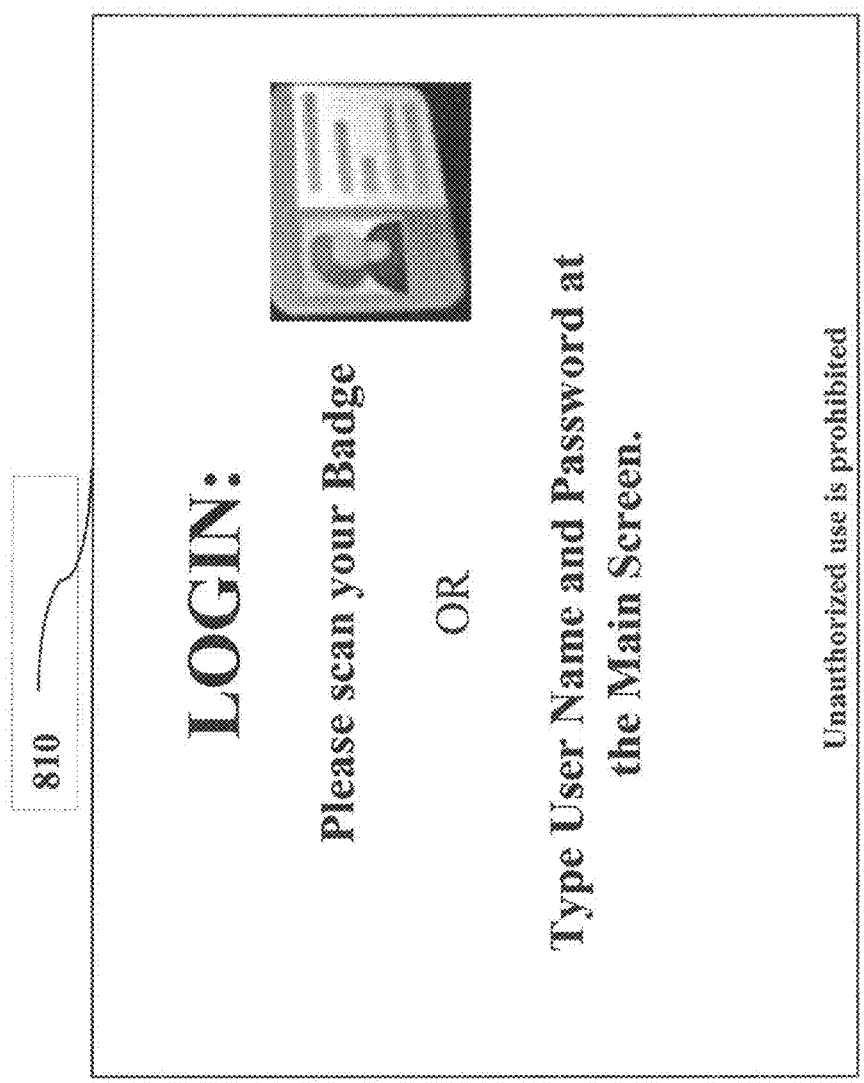
FIG. 8 is a diagram that illustrates an embodiment of a sign on screen for a mobile radiographic system according to the application.

FIG. 8 is a diagram that illustrates an embodiment of a sign on screen according to the application. Thus, when an attempt is made to operate the mobile x-ray imaging apparatus 100, a sign on screen 810 can be displayed to provide instructions to a user. As shown in FIG. 8, the single sign on screen 810 can provide instructions for sign on sign on and activate the mobile x-ray system 400 such as "LOGIN: Please scan your badge or type User Name and Password at the main screen." Exemplary embodiments of a pass key or ID badge can include but are not intended to be limited to a card reader such as a smart card, a magnetic stripe card, bar code data, or a proximity reader compatible with access technologies such as RFID, bluetooth, wireless communication device, a proximity card, a wireless smart card, a wiegand card, a magnetic reader device/card, an optical reader device/card, an infrared reader device/card, or biometric data such as fingerprints, eye scan or the like.

In one embodiment, the sliding detector locking device 600 can be moved to the unlocked position upon operator log in or sign onto the mobile x-ray apparatus 400. For example, a technician can use their ID badge to perform the sign on to the mobile radiographic system 100 by placing their ID badge in close proximity to a reader 150 (e.g., sign on reader). Verified identification using the single sign on reader 150 can provide authorization to access control of the mobile x-ray apparatus 400 and access (e.g., open) the lockable storage area 430. Preferably, after sign-on, additional swipes of the ID badge across reader 150 can operate to unlock the sliding detector locking device 600.

Figure 9A:
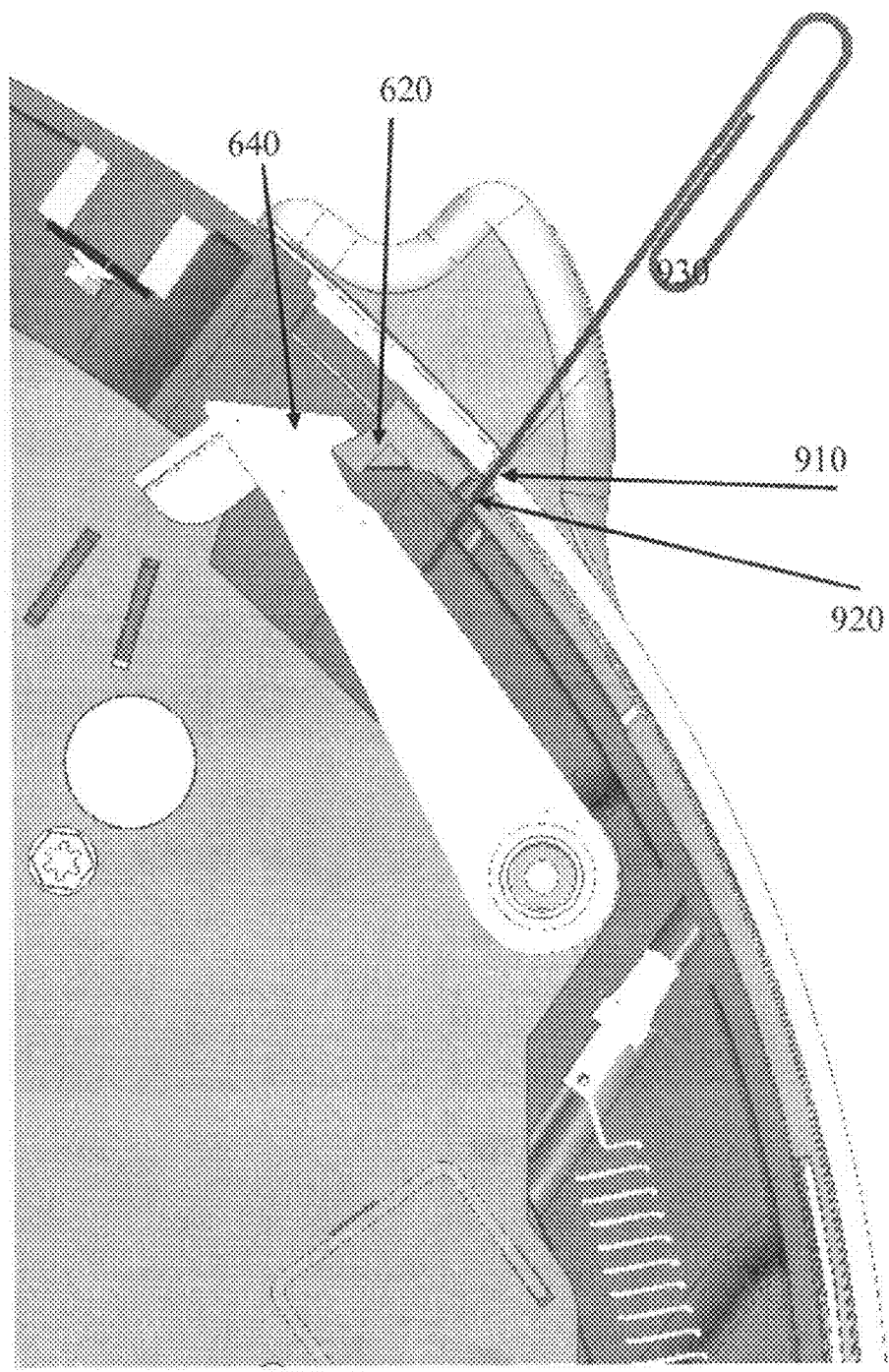
FIGS. 9A-9B are diagrams that show various views of an embodiment of a manual unlocking mechanism for a detector locking device for a mobile radiography unit according to the application.
Figure 9B:
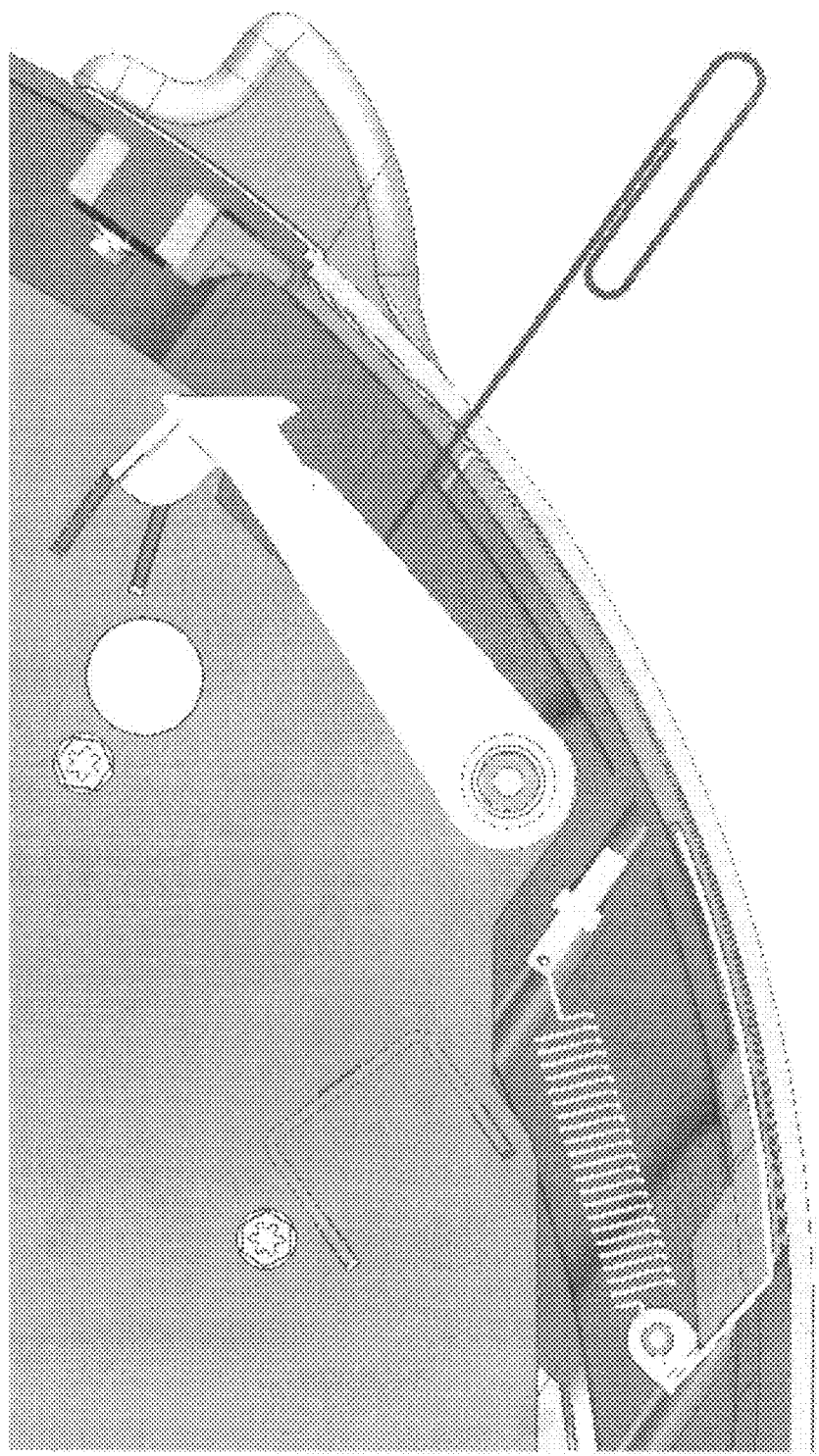

FIGS. 9A-9B are diagrams that show various views of an embodiment of a manual unlocking mechanism for a detector locking device for a mobile radiography unit according to the application. In one embodiment of the sliding detector locking device 600, the operator can unlock by physically moving the second engaging portion 640 to disengage and push the second engaging portion 640 to the unlocked position where the second engaging portion 640 is not engaged to the first engaging portion 620 as shown in FIG. 6A and the bar urging member 672 can move the sliding bar 610 along the surface of the moveable transport frame 420 to abut the stopper 650. As shown in FIGS. 9A-9B, an access hole (e.g. camouflaged) and a passage 920 through the sliding bar 610 can allow a rigid bar such a paper clip to pass through the surface of the movable transport base 420 and the sliding bar 610 and push the second engaging portion 640 from the engaged position shown in FIG. 9A to the unengaged position shown in FIG. 9B. Preferable the rigid bar 930 can strike an upper surface of the second engaging portion 640. Thus, the first urging member 630 can be overcome or when the first urging member 630 is not operational, the sliding detector locking device 600 can be moved to the first unlocked position by the bar 930. In one embodiment, the access hole 910 can be camouflaged by using an option rotatable cover over the access hole 910. Alternatively, a plurality of access holes 910 can be provided where only a single one of the access holes aligns to the passage 920. Alternatively, the passage 920 can be offset from the access hole 910 or the passage 920 can be shaped so that a specific angled rigid bar 930 or a prescribed shaped bar 930 can be required to be able to access the second engaging portion 640.

FIG. 10 is a diagram that illustrates an embodiment of a lockable detector storage area authorization screen according to the application. As shown in FIG. 10, a lockable detector storage area authorization screen 1000 can include a lockable storage selection 1010. The lockable storage selection 1010 can provide the operator with the capability of controlling access to one or more detector storage areas (e.g., portable detectors) to be carried on the mobile x-ray imaging apparatus 400. The lockable storage selection 1010 can provide controllable access to the lockable storage area 430.

As shown in FIG. 10, the lockable storage selection 1010 can also include exemplary selections such as lock all detectors, unlock detector holder(s), unlock large DR detector(s), unlock small DR detector(s), or lock all detectors. Alternatively, the lockable storage selection 1010 can provide similar securing capability for detector battery storage. Although FIG. 10 illustrates selectable (e.g., radio) buttons, embodiments according to the application are not intended to be so limited as other selectable GUI instantiations of operator actions can be used.

In one embodiment, a site administrator (e.g., user with special privileges) for a medical facility or the operator can be able to correlate various radiographic detector(s) 460 with each mobile x-ray system 400 as the operator places an individual removable DR detector or detector holder in the storage areas 430.

Although, selected embodiments of the sliding bar 610 can move manually to a locked position, embodiments according to the application are not intended to be so limited. In one embodiment, the operator can operate the second engaging portion 640 to engage the first engaging portion 620 by selecting a lock detector operator action on a display device of the mobile x-ray apparatus. For example, an electro-mechanical apparatus (e.g., solenoid) can be used to move the sliding bar 610 between exemplary positions shown in FIG. 6A and FIG. 6B, respectively. Accordingly, an operator can select lock/unlock operator actions (e.g., on display 110, 110') to move the first engaging portion 620 and the second engaging portion 640 to one or more engaged positions and back to an unengaged position.

In exemplary embodiments, a lockable detector storage area device was configured to move between a first position restricting removal of at least one detector and a second position allowing removal of at least one detector from a storage area of a mobile x-ray system. Alternatively, embodiments of lockable detector storage area devices can move between more than one or a plurality of different positions restricting removal of at least one detector and an unlocked position allowing removal all detectors from a storage area of a mobile x-ray system. Thus, embodiments of lockable detector storage area devices can be configured to selectively lock (or unlock) individual ones or various combinations of storage slots 342, 344, 346.

In one embodiment, the second arm 636 can include a plurality of spaced second engaging portions (e.g., 640) where each can have a first sloped face (e.g., 642) and a second securing face (e.g., 644) to provide a plurality of engaged positions with the first engaging portion 620 using a single sliding detector locking device. In this case, the unlocking movement caused by the first urging member 630 can be arranged to clear one engaged position or clear all engaged positions of the plurality of second engaging portions to return the sliding detector locking device to a first or unlocked position. Alternatively, the sliding bar 610 can be configured with a plurality of spaced first engaging portions (e.g., 620) to selectively operate with a single second engaging portion 640 on the second arm 636.

Figure 15A:
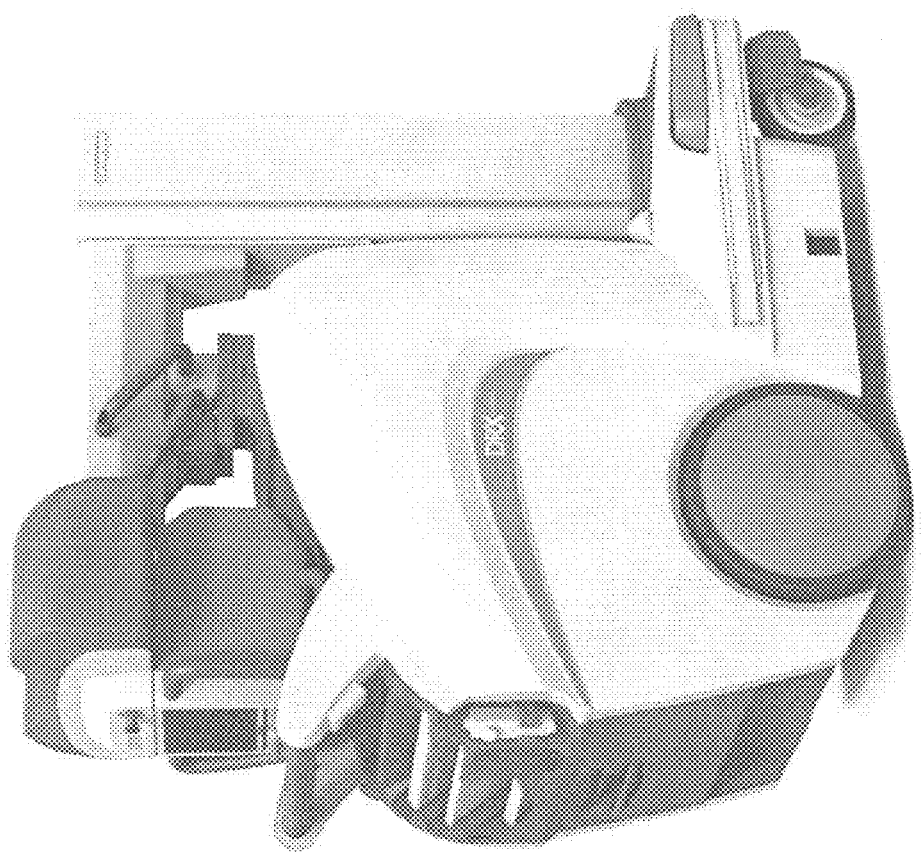
FIGS. 15A-15B are diagrams that illustrate an embodiment of a locking detector storage area for mobile radiographic system according to the application.
Figure 15B:
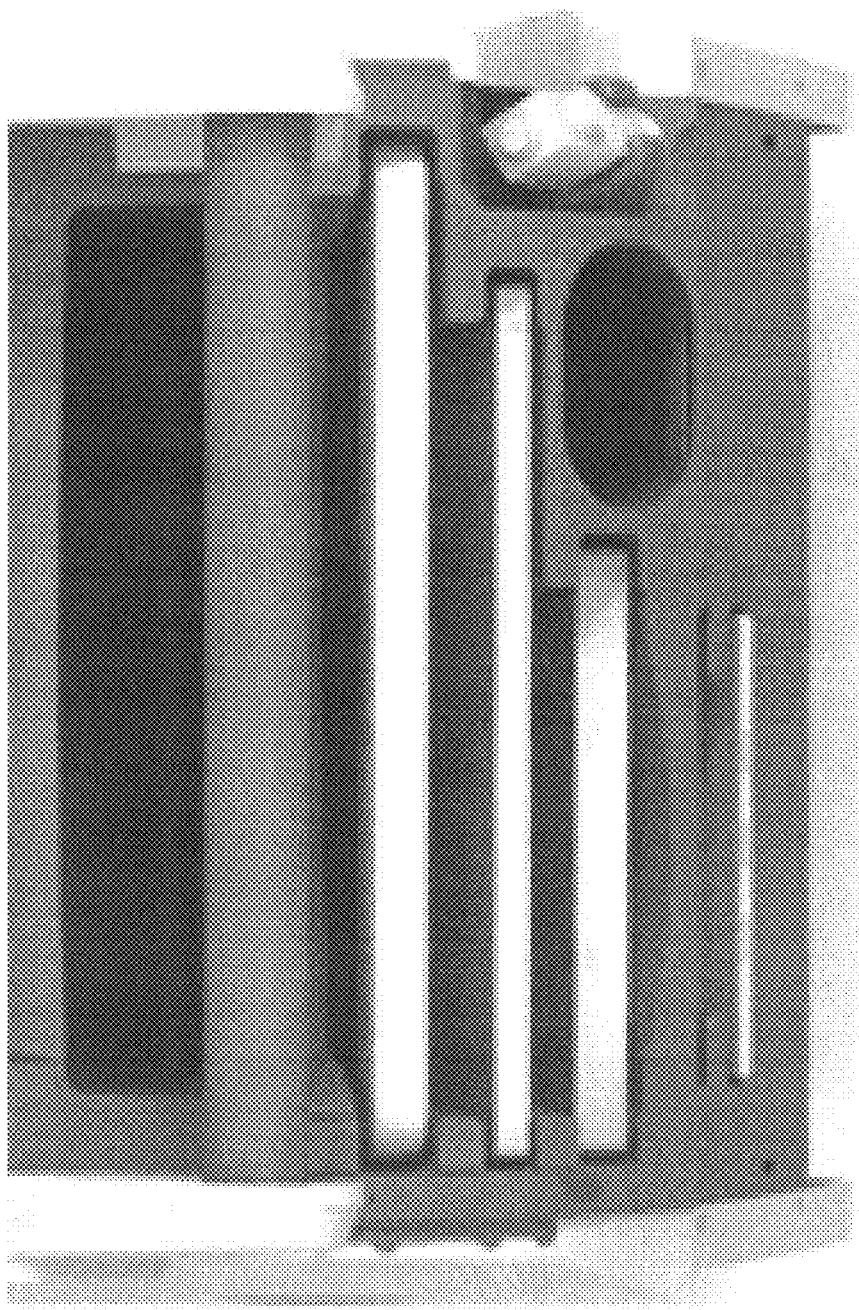

FIGS. 15A-15B are diagrams that respectively illustrate perspective and top views of another embodiment of a locking detector storage area for mobile radiographic system according to the application.

Embodiments according to the application can provide various advantages for a mobile x-ray apparatus including selectable secured access to visible multiple sized portable radiographic detectors. Embodiments according to the application can provide constant accessibility to secured portable detectors at the mobile x-ray apparatus where edges of the detectors are always accessible. Further, using recessed storage (e.g., of different sizes) can reduce a volume storage requirement for the secured detectors at the mobile x-ray apparatus, which can reduce a footprint of the mobile x-ray apparatus. Additionally, recessed storage for secured detectors (e.g., preferably displaced from each other) can provide a low profile extending above a surface of the mobile x-ray apparatus. However, recessed storage can be difficult to secure and even more difficult when secured using a staggered descending profile.

According to exemplary embodiments of the application, the first display 110 and the second display 110' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

According to embodiments of the application, the first display 110 and the second display 110' can provide capabilities/functionality to the mobile x-ray imaging apparatus 100 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam (In one embodiment, such a patient worklist can be automatically updated (e.g., synchronized to a master/hospital/doctor worklist) using a wired or wireless network/connection. In one embodiment, the mobile x-ray imaging apparatus 100 can highlight/indicate new exams (e.g., on the second display 110') upon receipt of the scheduled examination.); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile x-ray imaging apparatus 100 during transport, e.g., using a video camera located on the other side (e.g., front side of the mobile x-ray imaging apparatus 100).

Figure 12:
Figure 13:
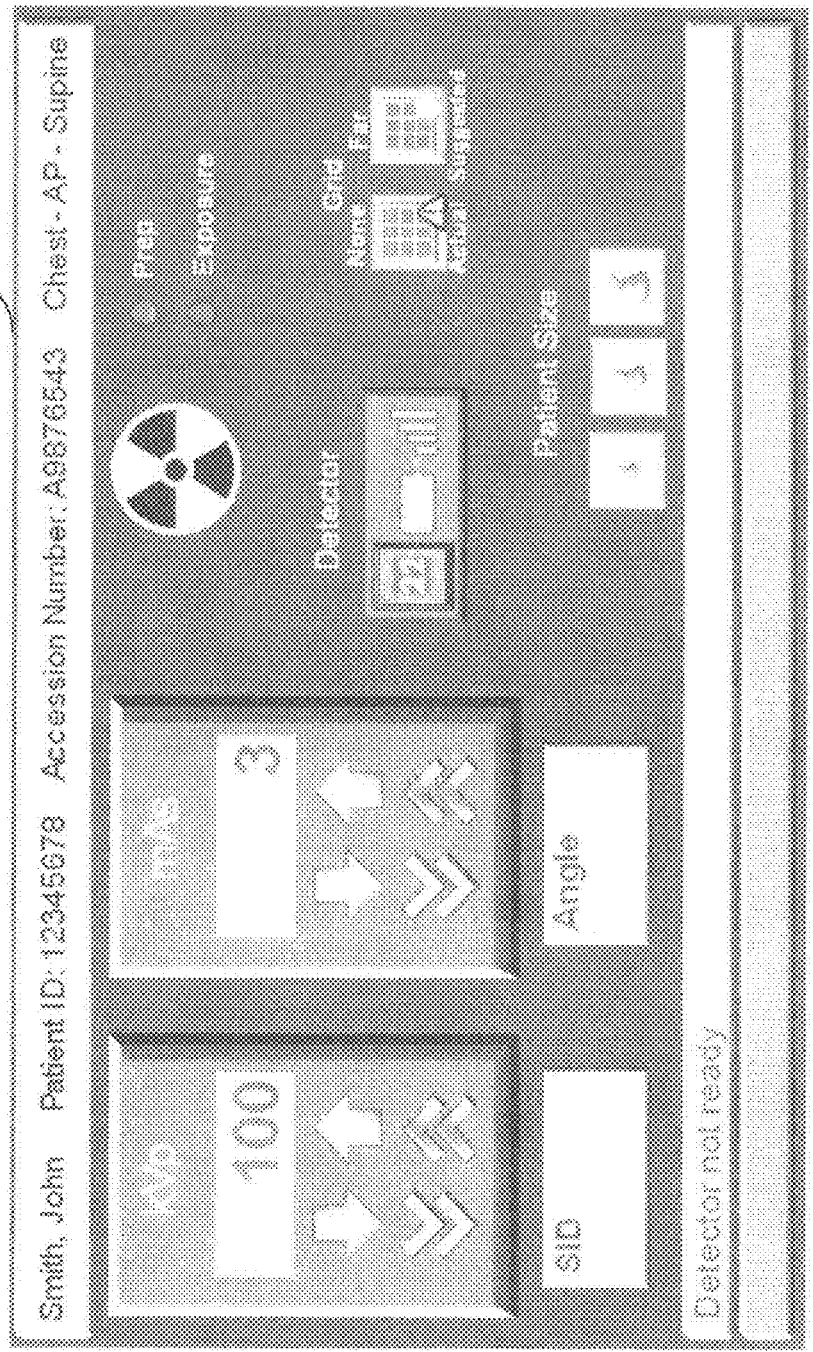
Figure 14:
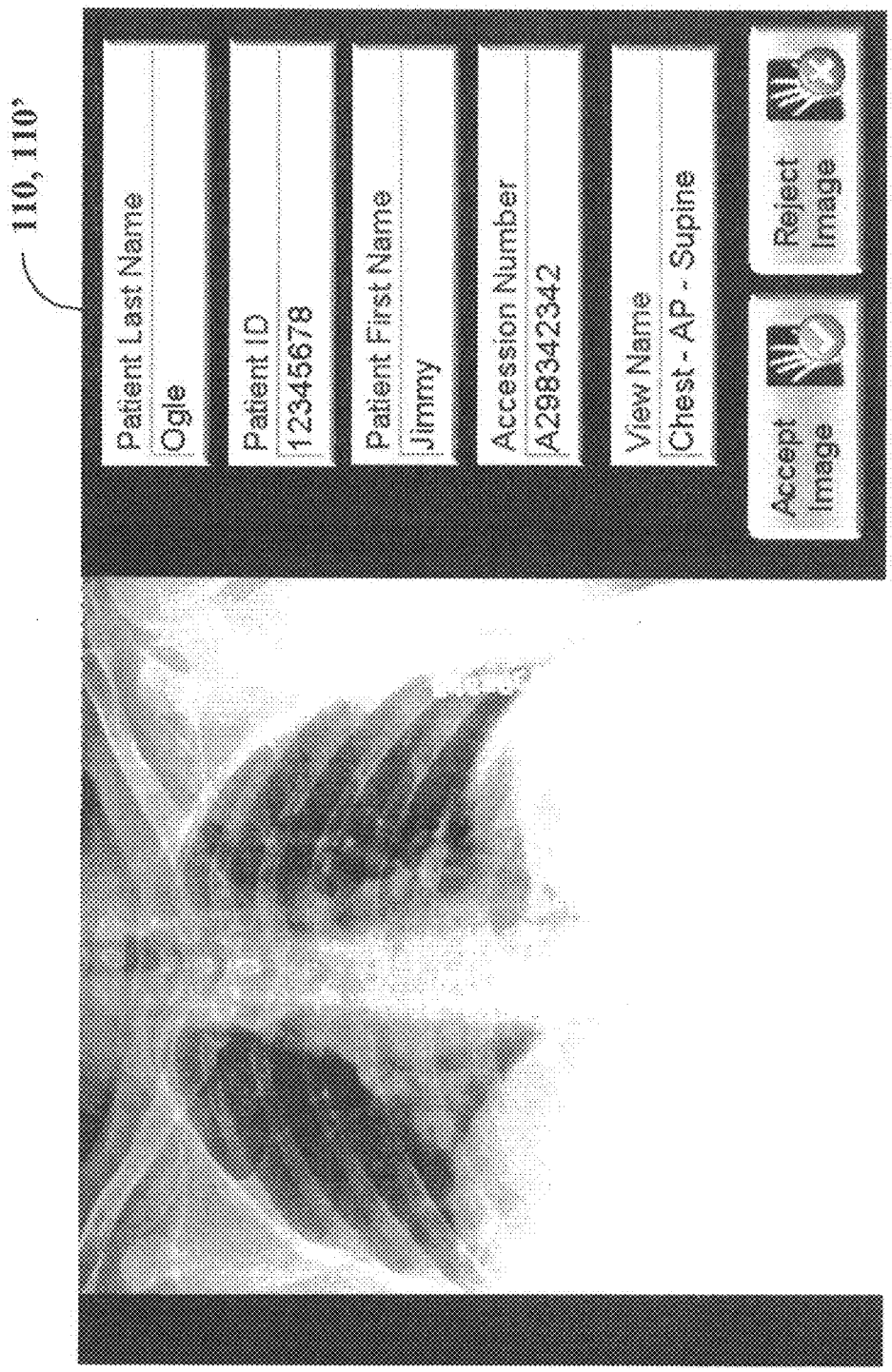

FIGS. 11-14 are diagrams that illustrate exemplary non-limiting representative functions illustrated on an embodiment of a second display of a mobile e-ray imaging apparatus. As shown in FIG. 11, an example of a work list is shown on a monitor of the second display 110'. As shown in FIG. 12, an example of a new examination/procedure information/requirement for that technician and/or patient is shown on a monitor of the second display 110'. As shown in FIG. 13, an example of x-ray source controls is shown on a monitor of the second display 110'. As shown in FIG. 14, an example of newly acquired image and patient information is shown on a monitor of the second display 110'.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

In one embodiment, the mobile radiographic imaging apparatus can be operated/controlled by programmed control logic in the first or second displays. For example, the programmed control logic can include a processor and display, an integrated computer system, or a portable computer and applications to operate thereon.

In one embodiment, a securing device for detector storage areas have a prescribed spaced relationship to detector(s) stored in a secured or locked position therein that can restrict removal by retractably blocking a travel path or path of movement taken by stored detectors during its' removal from the detector storage areas of mobile radiographic apparatus. Embodiments of a securing device can be positioned between a stored detector and an opening of a storage area or slot, above the opening of the storage area or slot, or within each storage area or each slot to block a travel path. Embodiments of a securing device physically can correspond to an outer surface of a stored detector to be physically positioned within a recess or detent in an outer surface of a stored detector(s) within a storage area or slot when in a locked position.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile radiography apparatus comprising:
a moveable transport frame;
an adjustable support structure coupled to the moveable transport frame;
an x-ray source coupled to the adjustable support structure; and
a lockable detector storage unit configured to securely store at least one radiographic detector at the mobile radiography apparatus, where the lockable detector storage unit comprises,
at least one recess configured to store the at least one radiographic detector, and
a securing device comprising,
a sliding member slidingly attached to the moveable transport frame to reciprocally move along a first direction,
a first engaging portion coupled to the sliding member,
an actuator configured to move between a first position and a second position,
a second engaging portion coupled to the actuator, where the second engaging portion is disengaged from the first engaging portion when the actuator is in the second position.

2. The mobile radiography apparatus of claim 1, the securing device further comprising:
a first secondary urging member to apply force to the securing device to move to the first position; and
another secondary urging member to apply force to the second engaging portion to move to the first position.

3. The mobile radiography apparatus of claim 1, where the lockable detector storage unit is configured to provide selectable access to a plurality of detectors at the lockable detector storage unit.

4. The mobile radiography apparatus of claim 1, where the at least one recess comprises a plurality of storage slots, where the securing device is configured to move between a first position to allow access to the at least one radiographic detector in the storage slots and a second position to secure the at least one radiographic detector in the storage slots.

5. The mobile radiography apparatus of claim 1, where the at least one recess comprises a plurality of storage slots, where the lockable detector storage unit is configured to provide selectable access to a plurality of different sized DR detectors or a DR detector holder in the plurality of storage slots.

6. The mobile radiography apparatus of claim 1, the securing device further comprising an access passageway through the securing device to allow access from outside the mobile radiography apparatus to a first surface of the second engaging portion.

7. The mobile radiography apparatus of claim 6, the access passageway is camouflaged or accessibly covered, and where a rigid shaped object can pass through the access passageway and move the second engaging portion to an unlocked position by contact with the first surface of the second engaging portion.

8. The mobile radiography apparatus of claim 1, further comprising a lockable detector storage control to control the lockable detector storage unit to releasably secure the at least one radiographic detector at the lockable detector storage unit.

9. The mobile radiography apparatus of claim 8, further comprising a proximity badge reader and the lockable detector storage control is enabled by placing an ID badge in operable range of the proximity badge reader.

10. The mobile radiography apparatus of claim 8, where the lockable detector storage control is an identification and password combination, an identification reader including a RFID, a proximity card, a wiegand card, a wireless smart card, a smart card, a magnetic stripe card, a bar code data or biometric data.

11. The mobile radiography apparatus of claim 1, where a first display is configured to provide a lockable detector storage unit control profile, where an operator selection at the lockable detector storage unit control profile moves the securing device between the first position, the second position and at least one additional position to selectively secure one, two or all of a plurality of slots in the at least one recess.

12. The mobile radiography apparatus of claim 1, where a first display provides an indication of allocation of the at least one radiographic detector when the at least one radiographic detector is assigned to the mobile x-ray radiography apparatus, where the allocation indication of the at least one radiographic detector can be set at the first display.

13. The mobile radiography apparatus of claim 1, where a curvature of the sliding member is configured to correspond to a curve of a surface of the moveable transport frame or an upper opening of a lockable detector storage area or an opening of the at least one recess.

14. The mobile radiography apparatus of claim 1, where the securing device is attached to the moveable transport frame or trapped between portions of the moveable transport frame.

15. The mobile radiography apparatus of claim 1, where the sliding member is an elongated bar extended in the first direction and configured to include a projection extended in a second direction to cover a upper opening of the at least one recess at a spaced relationship thereto.

16. The mobile radiography apparatus of claim 1, where the sliding member extends substantially from a top edge to a bottom edge of the at least one recess in a locked position, where the securing device is positioned at a left edge of the at least one recess, positioned at a right edge of the at least one recess or positioned between the left edge and the right edge of the at least one recess.

17. The mobile radiography apparatus of claim 1, comprising a first display to provide communication to the at least one radiographic detector; wherein the first display is configured to provide control of the x-ray source.

18. The mobile radiography apparatus of claim 17, where the first display and a second display are each configured to display obtained images and related data and a control panel to allow functions such as storing, transmitting, modifying, and printing of the obtained images, where the first display and the second display are each configured to view and/or modify x-ray exposure parameters, view and/or modify generator/source/technique settings, display image information, display patient information, display a patient worklist, display generator current values and controls to change those values, display detector selection, allow a user to select/activate a different detector, display recently acquired images and allow editing of those images, indicators or imaging procedure information, and where the adjustable support structure is configured to be adjustable in two dimensions or adjustable in three dimensions relative to the moveable transport frame.

19. A mobile x-ray radiographic apparatus comprising:
a moveable transport frame;
an adjustable support structure coupled to the moveable transport frame;
an x-ray source coupled to the adjustable support structure; and
a lockable detector storage unit configured to lockably store at least one portable detector at the mobile x-ray radiographic apparatus, where the lockable detector storage unit comprises,
  at least one recess configured to store the at least one remote digital detector, and
  a securing device comprising,
    an elongated bar slidingly attached to the moveable transport frame to reciprocally move along a first direction between a first position and a second position and configured to include at least one projection,
    a first engaging portion coupled to the elgonated bar;
    a second engaging portion, and
    an actuator coupled to and configured to move the second engaging portion,
  where the securing device is configured to allow access to the at least one recess in the first position, where the securing device is configured to secure the at least one recess in the second position, and where the second engaging portion is positioned to engage the first engaging portion when the securing device is in the second position.

* * * * *